(12) United States Patent
Smith et al.

(10) Patent No.: US 8,738,141 B2
(45) Date of Patent: May 27, 2014

(54) CONTACT ASSEMBLY FOR IMPLANTABLE PULSE GENERATOR AND METHOD OF USE

(75) Inventors: Alexander K. Smith, Chesterland, OH (US); Daniel N. Kelsch, Fairview Park, OH (US)

(73) Assignee: Greatbatch, Ltd., Clarence, NY (US)

( * ) Notice: Subject to any disclaimer, the term of this patent is extended or adjusted under 35 U.S.C. 154(b) by 547 days.

(21) Appl. No.: 13/081,836

(22) Filed: Apr. 7, 2011

(65) Prior Publication Data

US 2012/0259381 A1   Oct. 11, 2012

(51) Int. Cl.
*A61N 1/00* (2006.01)

(52) U.S. Cl.
USPC ............................................................ 607/46

(58) Field of Classification Search
USPC ..................................... 607/2, 46; 439/271
See application file for complete search history.

(56) References Cited

U.S. PATENT DOCUMENTS

| | | |
|---|---|---|
| 4,469,104 A | 9/1984 | Peers-Trevarton |
| 4,995,389 A | 2/1991 | Harris |
| 5,545,188 A | 8/1996 | Bradshaw et al. |
| 5,795,165 A | 8/1998 | Jarl |
| 5,899,930 A | 5/1999 | Flynn et al. |
| 6,498,952 B2 | 12/2002 | Imani et al. |
| 6,654,641 B1 | 11/2003 | Froberg |
| 6,662,035 B2 | 12/2003 | Sochor |
| 6,749,358 B2 | 6/2004 | Balsells |
| 6,878,013 B1 | 4/2005 | Behan |
| 6,895,276 B2 | 5/2005 | Kast et al. |
| 6,895,876 B2 | 5/2005 | Bergere |
| 7,070,455 B2 | 7/2006 | Balsells |
| 7,274,963 B2 | 9/2007 | Spadgenske |
| 7,537,474 B2 | 5/2009 | Deininger et al. |
| 7,654,843 B2 | 2/2010 | Olson et al. |
| 7,690,953 B2 | 4/2010 | Boyd et al. |
| 7,711,427 B2 | 5/2010 | Janzig et al. |
| 7,769,458 B2 | 8/2010 | Ries et al. |
| 7,890,175 B1 | 2/2011 | Rey et al. |
| 8,131,370 B2 | 3/2012 | Janzig et al. |
| 2003/0040780 A1 | 2/2003 | Haeg et al. |
| 2003/0179536 A1 | 9/2003 | Stevenson et al. |
| 2004/0167582 A1 | 8/2004 | Tvaska et al. |
| 2006/0004419 A1 | 1/2006 | Olbertz |
| 2006/0047322 A1 | 3/2006 | Naviaux |
| 2007/0202728 A1 | 8/2007 | Olson et al. |
| 2008/0071320 A1 | 3/2008 | Brase |
| 2008/0246231 A1 | 10/2008 | Sjostedt et al. |

(Continued)

FOREIGN PATENT DOCUMENTS

| | | |
|---|---|---|
| DE | 19917779 | 11/2000 |
| EP | 1062986 | 12/2000 |

(Continued)

OTHER PUBLICATIONS

European Search Report; Application No. EP 12 16 3521; Reference: PT02407EP; Application: Greatbatch Ltd.; Place of Search: Munich; Date of Completion of Search: Sep. 19, 2012.

(Continued)

*Primary Examiner* — Christopher D Koharski
*Assistant Examiner* — Nadia Ahmad
(74) *Attorney, Agent, or Firm* — Pearne & Gordon LLP

(57) ABSTRACT

A contact assembly for a medical device and, more specifically, to a header contact assembly for achieving electrical contact with an in-line IPG lead utilizing a contact structure such as a "toroidal spring in groove" device.

30 Claims, 8 Drawing Sheets

(56) References Cited

U.S. PATENT DOCUMENTS

| | | |
|---|---|---|
| 2008/0255631 A1 | 10/2008 | Sjostedt et al. |
| 2009/0017668 A1 | 1/2009 | Deininger et al. |
| 2009/0099620 A1 | 4/2009 | Rebentisch |
| 2009/0118778 A1 | 5/2009 | Biggs, Jr. et al. |
| 2009/0243756 A1 | 10/2009 | Stevenson et al. |
| 2009/0258519 A1 | 10/2009 | Dilmaghanian et al. |
| 2009/0312835 A1 | 12/2009 | Stevenson |
| 2010/0016928 A1 | 1/2010 | Zdeblick et al. |
| 2010/0109966 A1 | 5/2010 | Mateychuk et al. |
| 2010/0191299 A1 | 7/2010 | Ayzenberg |
| 2010/0274309 A1 | 10/2010 | Knipfer et al. |
| 2011/0029036 A1 | 2/2011 | Yamamoto et al. |
| 2011/0137414 A1 | 6/2011 | Litzke et al. |
| 2011/0184479 A1 | 7/2011 | Kast et al. |
| 2011/0282410 A1 | 11/2011 | Lim |
| 2012/0253424 A1 | 10/2012 | Smith et al. |

FOREIGN PATENT DOCUMENTS

| | | |
|---|---|---|
| JP | 54057101 | 5/1979 |
| JP | 10223346 | 8/1998 |
| WO | 0064535 | 11/2000 |
| WO | 2005014108 | 2/2005 |
| WO | 2005105207 | 11/2005 |
| WO | WO2011011223 | 1/2011 |
| WO | 2011017432 | 2/2011 |

OTHER PUBLICATIONS

European Search Report; Date of Report: Apr. 17, 2013; Reference: PT02775EP; Applicant: Greatbatch Ltd.; Application No. EP 13151690.8-1652; Place of Search: Munich; Date of Completion of Search: Apr. 11, 2013.

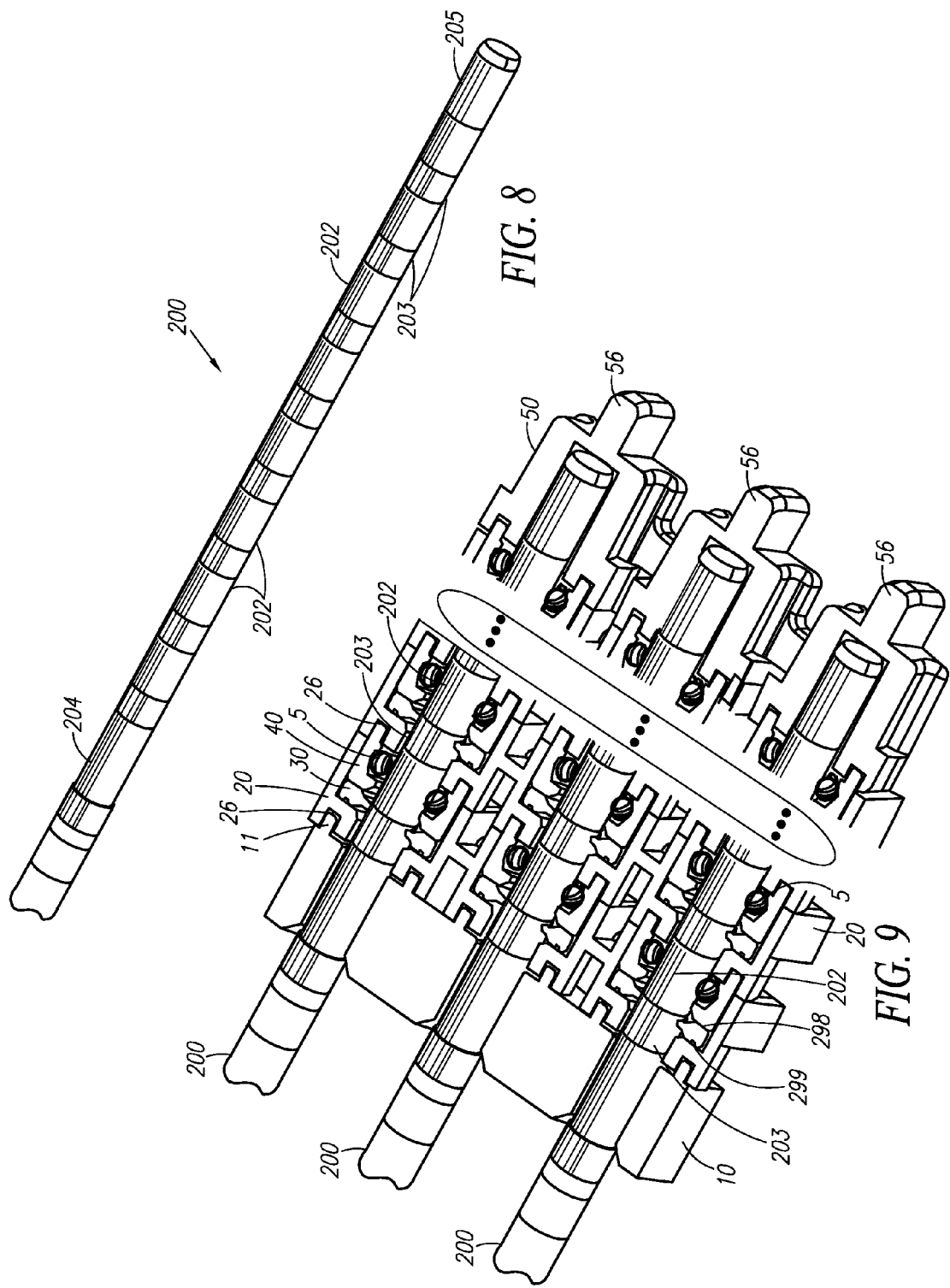

CONTACT ASSEMBLY FOR IMPLANTABLE PULSE GENERATOR AND METHOD OF USE

FIELD OF THE INVENTION

This application relates generally to a contact assembly for a medical device and, more specifically, to a header contact assembly for achieving electrical contact with an in-line IPG lead and utilizing a "toroidal spring in groove" structure.

BACKGROUND OF THE INVENTION

Medical devices have been implanted in patients to perform a variety of tasks. For example, programmable pulse generating systems are used to treat chronic pain by providing electrical stimulation pulses from an epidural electrode array placed near a patient's spine. Such Spinal Cord Stimulation (SCS) is useful for reducing pain in certain populations of patients. SCS systems typically include one or more electrodes connected to one or more connectors of an External Pulse Generator (EPG) or an Implanted Pulse Generator (IPG) via leads. In the case of an EPG, the lead must be connected to the EPG via an exit from the body. The pulse generator, whether internal or external, generates pulses that are typically delivered to the dorsal column fibers within the spinal cord through the electrodes which are implanted along or near the dura of the spinal cord. In a typical situation, the attached leads exit the spinal cord and are tunneled around the torso of the patient to a subcutaneous pocket where the IPG is implanted, or the wires exit the patient for connection to the EPG.

U.S. Pat. Nos. 7,537,474 and 6,895,876, incorporated herein by reference, disclose a connector solution for an implantable pulse generator (IPG) utilizing a coiled spring inside a contact block. The ends of the spring are welded together yielding a torus shape through which the in-line lead is inserted. The spring coils cant to conform to the contact ring of an IPG lead, thus making electrical contact. Each coil which contacts both the lead and the block forms a separate redundant electrical contact.

However, more accurate positioning of seals and electrical contact locations than are current available would be desirable. Furthermore, it would be useful to provide IPG devices with multiple lead ports that have contact stacks that are assembled as a single unit, and tested in a single fixture before final assembly of the IPG, to determine that all channels have electrical continuity to inserted pin(s) that represents a connection end of a stimulation lead.

SUMMARY OF THE INVENTION

Provided are a plurality of embodiments the invention, including, but not limited to, a contact assembly for an implantable medical device comprising: a first component forming an interior open portion therethrough, the first component having a first contact block receiving portion; a compliant insulating seal having a seal bore therethrough and being entirely contained within the interior open portion of the first component; a conductive contact block having a first side received by the first contact block receiving portion of the first component and in contact with the seal, the contact block also having a second side and a contact portion on a surface thereof and further having an interior open portion; and a second component having a second contact block receiving portion for receiving the second side of the contact block, the second component also having a bore therein, wherein the contact assembly is arranged for receiving a pin through the first component, through the bore of the seal, through the interior open portion of the conductive contact block, and into the bore of the second component, such that a conductive portion of the pin is provided in electrical contact with the conductive contact block when the pin is seated in the contact assembly.

Also provided is a contact assembly for an implantable medical device having at least 24 stimulation channels, the contact assembly for connecting to a plurality of pins each having a plurality of separate electrical contact surfaces, the contact assembly comprising: a plurality of conductive contact devices each adapted for electrically contacting one of the contact surfaces of one of the plurality of pins; and a plurality of conductive contact blocks each having an interior open portion adapted for receiving a corresponding one of the plurality of conductive contact devices in electrical contact therewith.

In the above contact assembly, the conductive contact blocks are arranged into a series of rows such that each one of the rows has an equal number of contact blocks arranged side-by-side, and the contact blocks are arranged such that each one of the contact blocks of one row are arranged with a corresponding one of the contact blocks of a subsequent and/or previous row to form a plurality of columns of contact blocks such that the interior open portions of the contact blocks of any given column are axially aligned to receive one of the plurality of pins.

Furthermore, the above contact assembly is organized such that at least 24 of the contact blocks are arranged to support at least 2 of the pins for providing the at least 24 stimulation channels.

Still further provided is a contact assembly for an implantable medical device comprising: a plurality of stacking components each forming an interior open portion therethrough, each of the stacking components having a first contact block receiving portion on a first side and also having a second contact block receiving portion on a second side; a plurality of compliant seals, each of the seals having a seal bore therethrough and being entirely contained in the interior open portion of one of the stacking components; and a plurality of conductive contact blocks each having a first side for being received by the first contact block receiving portion of one of the stacking components and/or having a second side for being received by the second contact block receiving portion of another one of the stacking components, each one of the contact blocks having an interior open portion adapted for receiving one of the plurality a conductive contact devices therein.

In the above contact assembly, the plurality of the stacking components are arranged in a series of rows, and for each stacking component in one row following a preceding stacking component in a previous row, the first contact block receiving portion is mated with the first side of one of the plurality of contact blocks having its second side mated with the second contact block receiving portion of the preceding stacking component in the previous row.

Also provided is a contact assembly for an implantable medical device comprising: a setscrew block having a bore therethrough forming a first end of the assembly; a plurality of stacking components each forming an interior open portion therethrough, each of the stacking components having a first contact block receiving portion on a first side and also having a second contact block receiving portion on a second side; a plurality of compliant seals, each of the seals having a seal bore therethrough and being entirely contained in the interior open portion of one of the stacking components; a plurality a conductive contact devices; a plurality of conductive contact blocks each having a first side for being received by the first contact block receiving portion of one of the stacking components and/or having a second side for being received by the second contact block receiving portion of another one of the stacking components, each one of the contact blocks having a contact portion on a surface thereof and having an interior open portion adapted for receiving one of the plurality a conductive contact devices therein; and an end cap including a bore forming a second end of the assembly.

Further provided is a contact assembly for an implantable medical device comprising: a stacking component forming a plurality of interior open portions therethrough, each interior open portion having a corresponding contact block receiving portion; a plurality of compliant seals having a seal bore therethrough, each of the seals being entirely contained within a corresponding one of the interior open portions of the first stacking component; a plurality of conductive contact blocks each for mating with one end of a corresponding one of the contact block receiving portions and having a contact portion on a surface thereof, wherein each one of the conductive contact blocks has an interior open portion therein; and a setscrew block having a plurality of setscrew bores therethrough such that each setscrew bore corresponds to one of the interior open portions of the stacking component.

In the above contact assembly, each one of the stacking component interior open portions is formed in alignment with the seal bore of the corresponding seal, the interior open portion of the corresponding contact block, and the corresponding setscrew bore to form a continuous axial chamber adapted for receiving a respective pin inserted from outside of the contact assembly, with the respective pin having a contact surface portion thereon for electrically connecting to the respective contact block.

Also provided is a contact assembly for an implantable medical device comprising: a setscrew block having a plurality of setscrew bores therethrough forming a first end of the assembly; a plurality of stacking components arranged into a series of rows, each one of the stacking components having a plurality of interior open portions therethrough with each one of the interior open portions being associated with one of the setscrew bores and forming a first contact block receiving portion on a first side and also forming a second contact block receiving portion on a second side; a plurality of compliant seals each having a seal bore therethrough and each being provided in a corresponding one of the interior open portions of a corresponding one of the stacking components; a plurality a conductive contact devices; a plurality of conductive contact blocks each having a first side for being received by one of the first contact block receiving portions of one of the stacking components and/or having a second side for being received by one of the second contact block receiving portions of another one of the stacking components, each one of the contact blocks having a contact portion on a surface thereof and having an interior open portion adapted for receiving one of the plurality of conductive contact devices therein, wherein each one of the interior open portions of each one of the conductive contact blocks is associated with one of the setscrew bores; and an end cap including a plurality of end bores forming a second end of the assembly, each one of the end bores being associated with one of the setscrew bores.

The above contact assembly is adapted for receiving a plurality of pins, each one of the pins for being inserted into an associated one of the setscrew bores and through the interior open portions of the stacking components, the seal bores, and the interior portions of the contact blocks associated therewith, with the end of each pin entering the associated one of the end bores.

Further provided is a contact assembly for an implantable medical device for providing at least 24 stimulation channels, the contact assembly comprising: a setscrew block having a plurality of setscrew bores therethrough forming a first end of the assembly; a plurality of stacking components arranged into a series of rows, each one of the stacking components having a plurality of interior open portions therethrough with each one of the interior open portions being associated with one of the setscrew bores and forming a first contact block receiving portion on a first side and also forming a second contact block receiving portion on a second side; a plurality of compliant seals each having a seal bore therethrough and each being entirely contained in a corresponding one of the interior open portions of a corresponding one of the stacking components; a plurality of at least 24 conductive contact devices; a plurality of at least 24 conductive contact blocks each having a first side for being received by one of the first contact block receiving portions of one of the stacking components and/or having a second side for being received by one of the second contact block receiving portions of another one of the stacking components, each one of the contact blocks having a contact portion on a surface thereof and having an interior open portion adapted for receiving one of the plurality of conductive contact devices therein, wherein each one of the interior open portions of each one of the conductive contact blocks is associated with one of the setscrew bores; and an end cap including a plurality of end bores forming a second end of the assembly, each one of the end bores being associated with one of the setscrew bores.

In the above contact assembly, the plurality of the stacking components are arranged in a series of rows such that for each stacking component in one row following a preceding stacking component in a previous row, the first contact block receiving portion is mated with the first side of one of the contact blocks having its second side mated with the second contact block receiving portion of the preceding stacking component in the previous row.

Also in the above contact assembly, the second contact block receiving portion of the first contact block in the series mates with an inner end of the setscrew block, and the end cap mates with the second end of the contact block having its first end mated with the last stacking component in the series.

Further, the contact assembly is adapted for receiving a plurality of pins, each one of the pins having a plurality of contact surface portions thereon, and each one of the pins for being inserted into an associated one of the setscrew bores and through the interior open portions of the stacking components, the seal bores, and the interior portions of the contact blocks associated therewith, with the end of each pin entering the associated one of the end bores, and with each of the conductive contact devices being adapted for electrically connecting to a corresponding one of the contact surface portions of one of the pins.

Still further provided is a system for stimulating a stimulation region of a patient comprising an IPG including a contact assembly as described above connected to the IPG using a connector assembly.

Further provided are a system and a method of therapy, such as one using the above system, for example.

Also provided are additional embodiments of the invention, some, but not all of which, are described hereinbelow in more detail.

BRIEF DESCRIPTION OF THE DRAWINGS

The features and advantages of the examples of the present invention described herein will become apparent to those skilled in the art to which the present invention relates upon reading the following description, with reference to the accompanying drawings, in which:

FIG. 8 shows an example electrode pin;

FIG. 9 shows a partial view of the cross section of the example contact assembly of FIG. 7;

DETAILED DESCRIPTION OF THE EXAMPLE EMBODIMENTS

Provided is a unique way of achieving electrical contact with an in-line IPG lead while applying a widely accepted "toroidal spring in groove" contact assembly. A contact stack assembly is provided that is composed of a thermoplastic stacker component that houses a silicone seal followed by an electrically conductive (e.g., metal) contact block that houses a toroidal spring in a groove, e.g., an industry standard solution. The function of the silicone seal component is to isolate neighboring electrical contacts. A flat portion of the contact block protrudes from the stack and facilitates welding of an electrically conductive lead or wire intended to route to/through a hermetic feed-through. The stack and attached conductor wire is intended to be completely embedded in a nonconductive material such as thermoplastics, epoxy, or silicone. This nonconductive material is used to prevent fluid ingress into seams between the stackers.

The design provides a nonconductive stacker part to contain the seal and contact elements. The conductive contact block serves to align the nonconductive stackers forming an interlocking stack. Accurate positioning of seals and electrical contact locations in this arrangement is possible because the overall length tolerance of the stacker component is the only factor in end-to-end location variability. The stacker can be produced from a well centered micro-molding process that is capable of extremely tight tolerance control so that stacks consisting of as many as 12 contacts or more can be applied while maintaining acceptable accuracy.

The stack contact assembly allows IPG devices with multiple lead ports to have contact stacks that are assembled as a single unit and tested in a single fixture before assembly to determine that all channels have electrical continuity to an inserted pin that represents the connection end of a stimulation lead.

Figure 1:
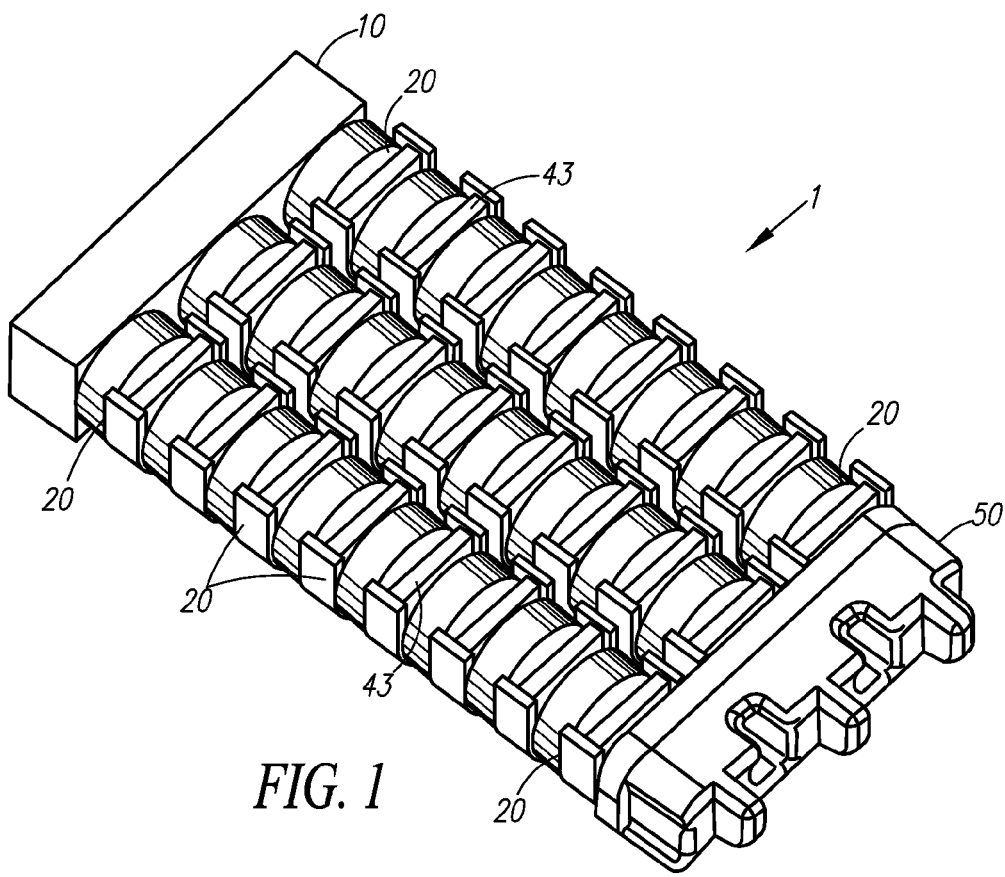
FIG. 1 shows an example embodiment of a contact assembly.
Figure 2:
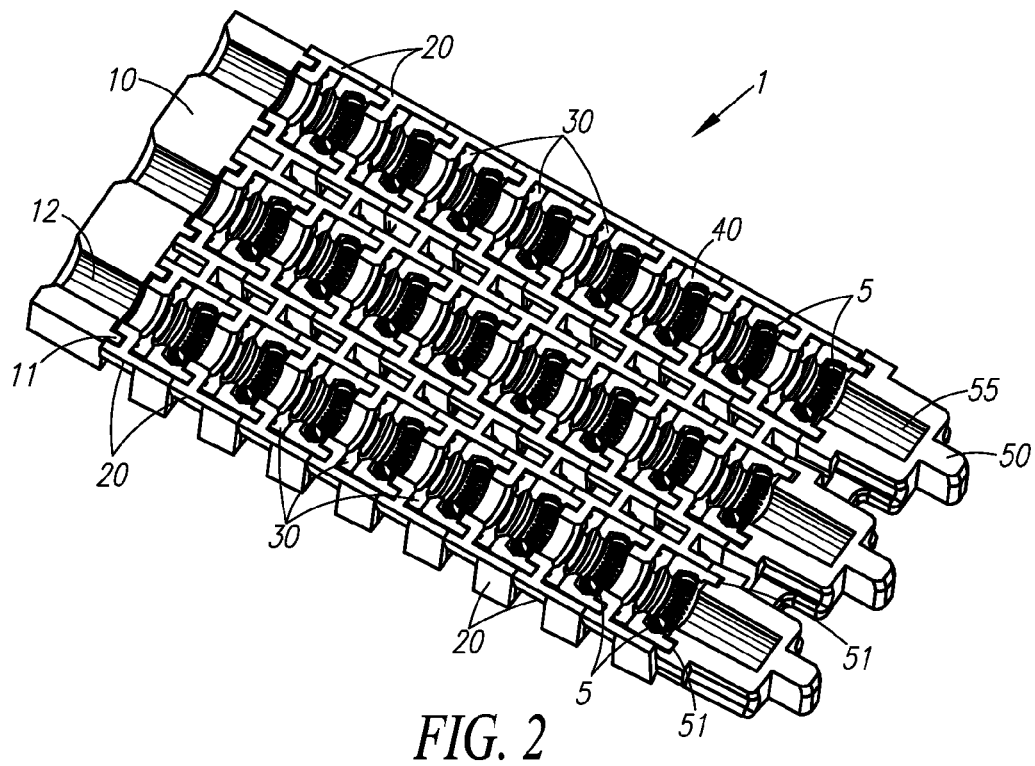
FIG. 2 shows a cross section of the example contact assembly of FIG. 1 flipped over.
Figure 3:
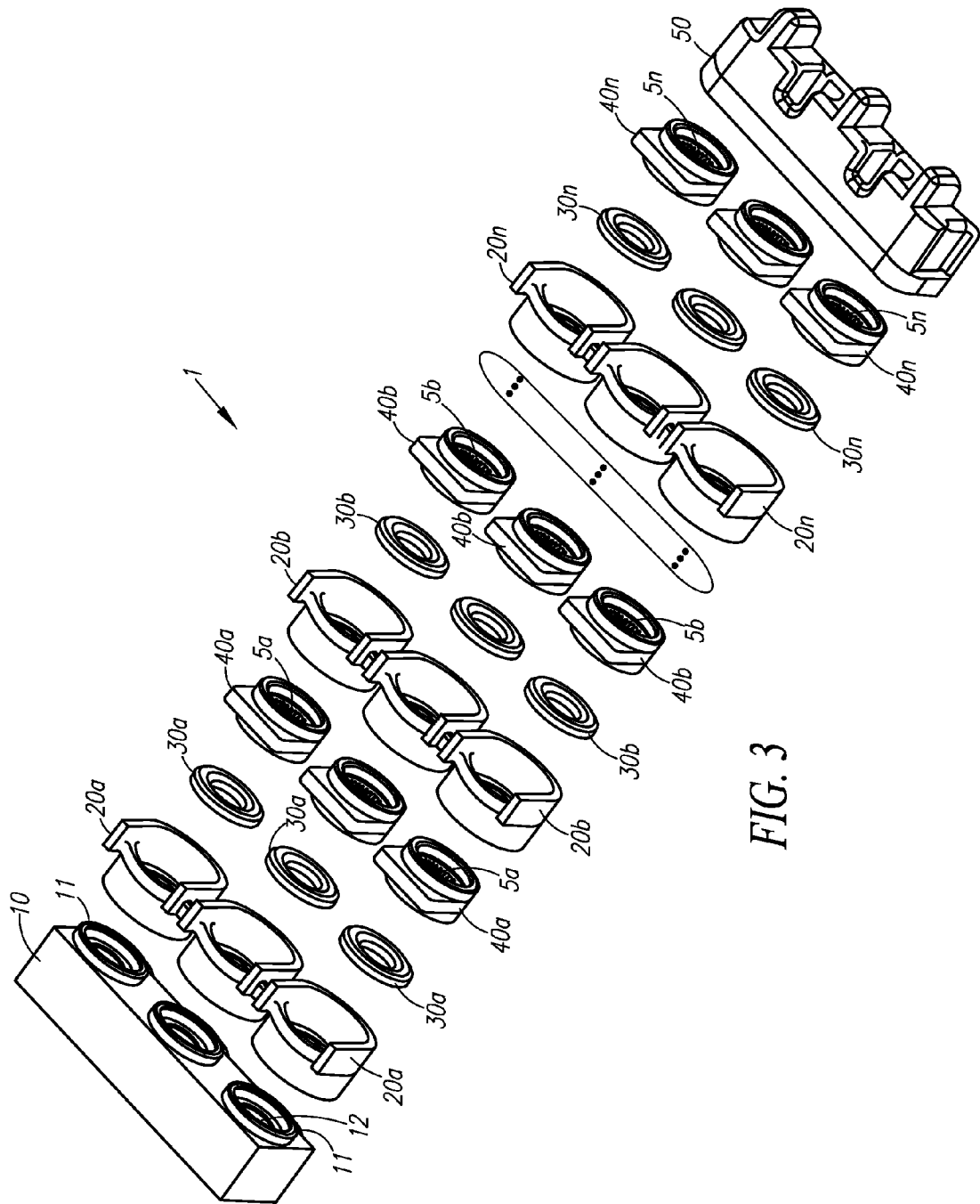
FIG. 3 shows a partial expanded view of example components of the example contact assembly of FIG. 1.
Figure 4:
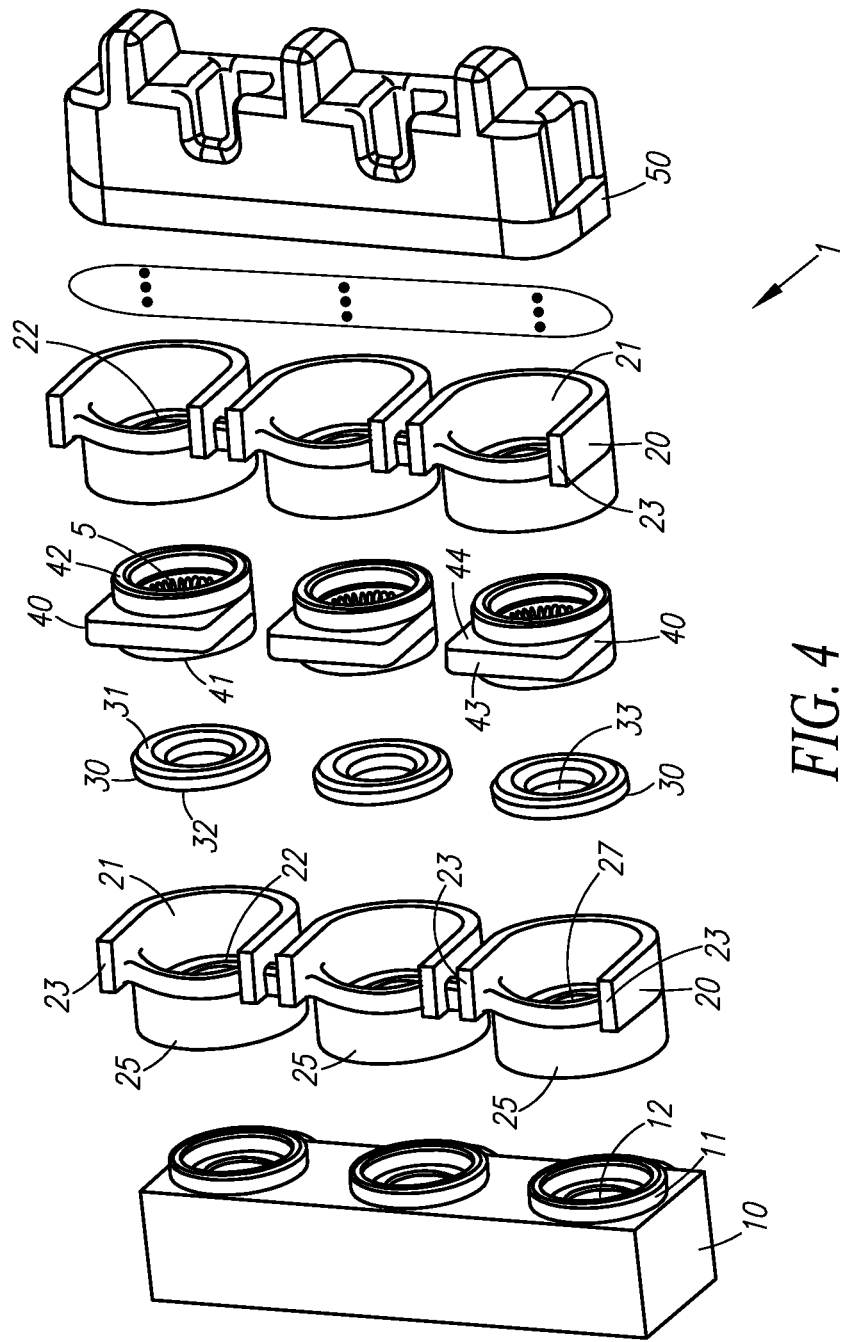
FIG. 4 shows another view of the partial expanded view of example components of the example contact assembly of FIG. 1.
Figure 5:
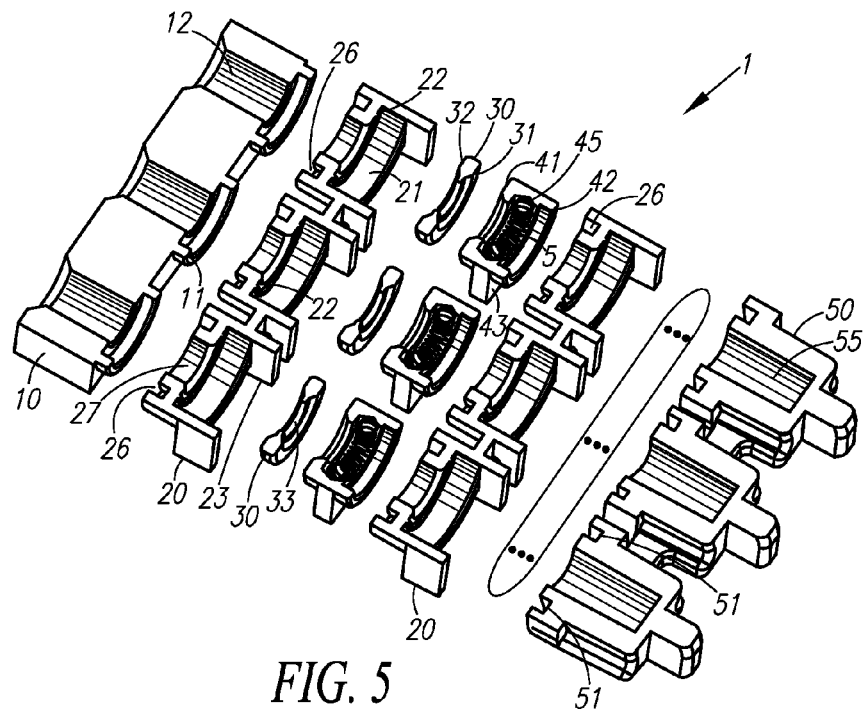
FIG. 5 shows cross sections of the components of the partial expanded view of FIG. 4 flipped over.

FIG. 1 shows an example schematic of the contact assembly with FIG. 2 showing a cross section of the assembly, FIGS. 3-4 show exploded views of the individual components of the contact assembly, and FIG. 5 shows a cross-section of the individual components of the assembly.

In FIG. 3, the reference numbers of the various components are arranged in "rows", with the reference numbers having a row indicator, the first row being row "a", the second row being row "b", and the final row being row "n", for an arbitrary number of "n" rows.

In reference to FIGS. 1-2 and 4-5, the example contact assembly is comprised of a setscrew block 10 and an end cap 50 covering opposite ends of the contact assembly. A plurality of thermoplastic stacker components 20 are shown provided between the setscrew block 10 and the end cap 50. For the example embodiment, there is one stacker component per "row". Each of the thermoplastic stacker components is associated with a set of conductive contact blocks 40 (three per row are shown in the example embodiment, representing three "columns"), a set of corresponding seals 30 (3 per row in the example), and a set of springs 5 (again, 3 per row in the example). For this example embodiment shown in the figures, there are eight sets of stacker components (i.e., forming 8 "rows") with each stacker component (and thus each row) associated with a set of three contact block/seal/spring groupings (i.e., three "columns"). Of course, alternative embodiments could utilize alternative numbers of contact blocks (i.e., different numbers of rows), and each contact block might be associated with a different number of contact block/seal/spring groupings (i.e., different numbers of columns), such as using a single grouping, or two, four, five, or more groupings, depending on the desired implementation. Alternatively, the stacker components could be comprised of separate sub-components each associated with one of the contact blocks (hence for the example, there would be three sub-components).

FIG. 4 shows an exploded view of a top portion of the example contact assembly, whereas FIG. 5 shows a cross section of the exploded view flipped over (with the top shown facing down into the page). These figures show a stacker component 20 with an associated three contact blocks 40, three seals 30, and three springs 5 (the choice of 3 being merely the particular solution for the example embodiment, with the choice of 2 being an alternative solution being contemplated, among others).

The stacker component 20 is comprised, for example, of 3 pairs of block tabs 23 each pair of tabs 23 being associated with a curved surface 21 and an inner surface 22 formed around a cylindrically shaped hole/void/27 provided through the stacker component. The stacker component 20 has, for example, three holes (bores) 26, for receiving correspond pins 200 as described below (see FIGS. 7-9). Note that in the example of the figures, the curved surface 21 is deeper at the bottom than at the top, as part of the curved surface at the bottom merges with at least part of the sides of the block tabs 23, which are at least partially flat.

For any given stacker component, each hole 27 along with the associated curved surface 21, associated inner surface 22, and associated pair of tabs 23 are adapted for receiving a corresponding seal 30, with one side 32 of the seal for contacting the inner surface 21, which, along with inner surface 22, holds the seal in place. Each seal 30 has a hole 33 formed in its center that is aligned with the associated hole 27 for receiving the corresponding pin 200.

For any given stacker component, each pair of tabs 23 and their associated curved surface 21 are also adapted to receive part of a contact block 40. The pair of block tabs 23, along with the curved inner surface 21 and the associated seal 30 form a receptacle for receiving (mating) with the part of the corresponding contact block 40 and at least laterally holding it in place. On an opposite side of the stacker component 20 is provided, for example, three rings 25 each of which each is formed with the hole 27 therethrough and a receiving groove 26 (see FIG. 5). The receiving grooves 26 are each adapted to receive a cylinder portion 42 of an opposite side of a contact block 40, and the grooves 26 can also, where appropriate, mate with the corresponding three ring tabs 11 of the setscrew block 10.

Figure 6:
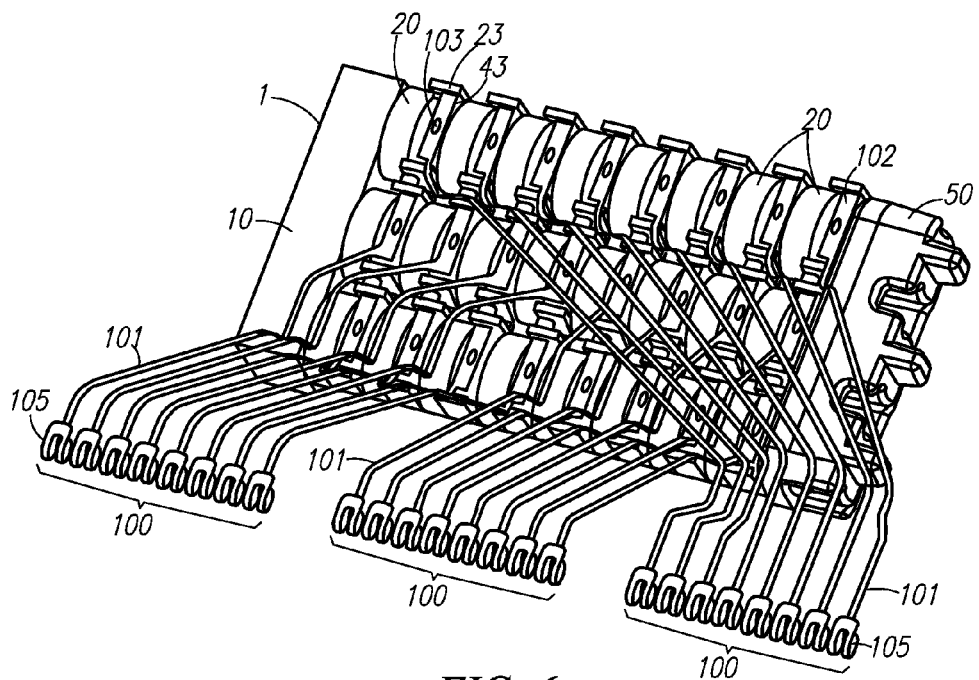
FIG. 6 shows the example contact assembly of FIG. 1 with connecting leads installed.

Each contact block 40 has a conductive contact surface 43 on contact tab 44 that, when paired with the associated stacker component 40, is exposed between the associated pair of block tabs 23 of the stacker component, the conductive contact surface 43 being exposed for electrically connecting to a contact lead 102 (see FIG. 6). Each contact block 40 has a first cylindrical portion 41 for being received by one of the curved surfaces 21 of a stacker component and placed against a corresponding seal 30. Each contact block 40 also has a second cylindrical portion 42, for being received by either the curved inner surface 21 of a corresponding contact block (of a subsequent row), or a corresponding cylindrical shaped groove 51 of the end cap. Also, each contact block 40 also has an interior hole and a hollowed out interior portion with a groove for holding a corresponding spring 5 as a contact device for contacting a conductive portion 202 of the pin 200. Each spring 5 is formed in a ring (donut) shape of conductive material with a void in its center (for receiving the associated pin 200) and is in electrical contact with its corresponding contact block to ensure electrically conductivity.

Figure 7:
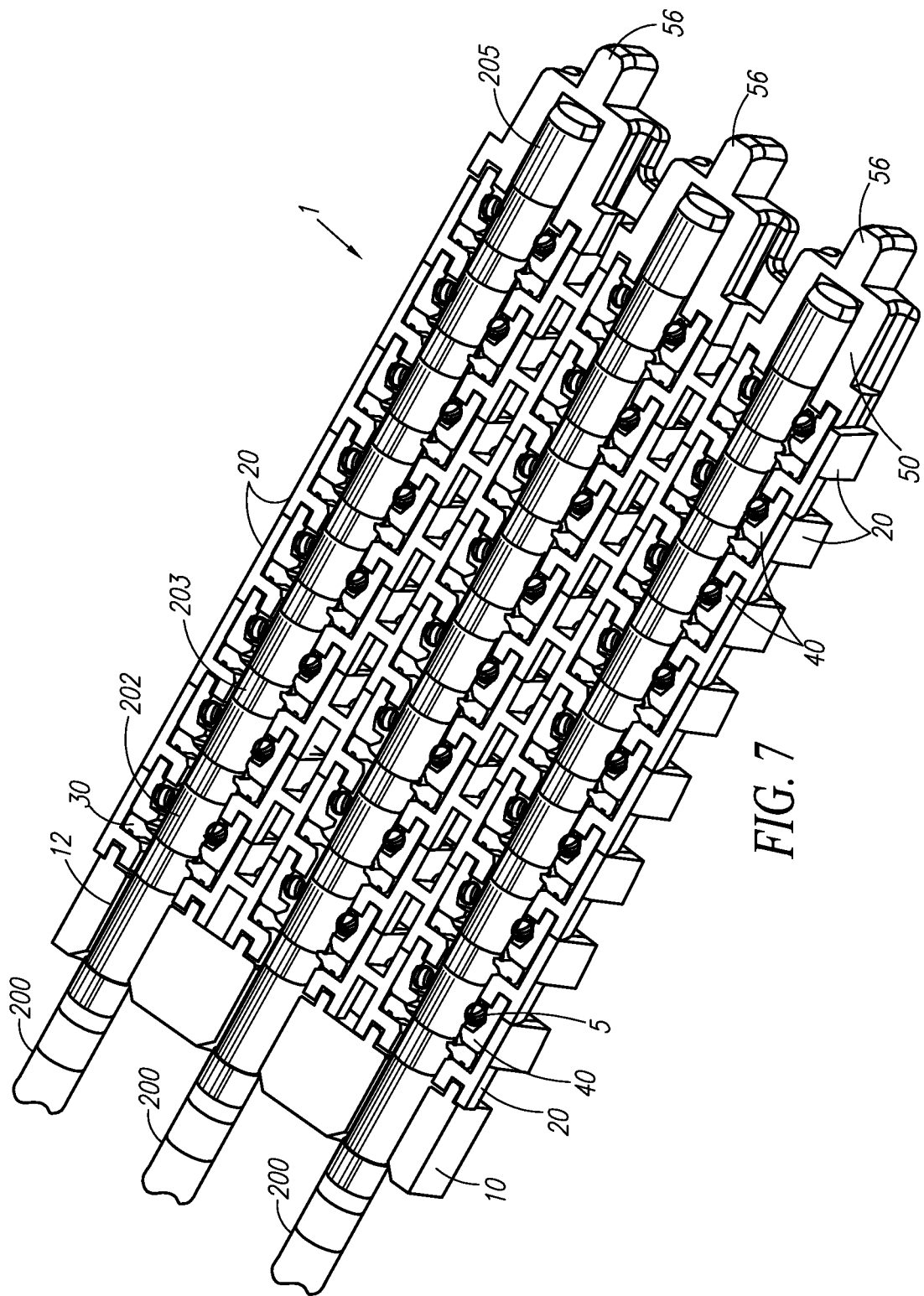
FIG. 7 shows a cross section of the example contact assembly of FIG. 1 flipped over, with connector pins inserted.

The springs 5 are, in the example embodiment, torsion springs formed into a ring (a toroid/"donut" shape) having a space or hole in the center for receiving the corresponding electrode pin 200 (see FIGS. 7, 9). When the pins 200 are inserted therethrough, the springs flex (cant) against and in contact with a corresponding conductive ring 202 on the surface of the pin 200 to make electrical contact with the conductive ring 202, as illustrated in FIGS. 7 and 9. Alternative means of providing electrical contact between the pin conductive rings and the contact blocks could also be provided, such as by using metal tabs or different spring mechanisms, if desired. Alternatively, the contact block could have the contact device directly incorporated into the structure of the interior portion of the contact block, such as by providing conductive tabs, bumps, or other structures integrated or formed in the contact block for directly contacting the conductive portion 202 of the pin 200.

The first cylinder portion 41 of any given contact block 40 has a flat surface that is adapted to be provided in contact with a second surface 31 of a corresponding seal provided in the corresponding contact holder 25. As described above, in most situations the second cylindrical portion 42 of each contact block is received by (mates with) the corresponding receiving groove 26 of a following stacker component 20 which acts to "cap" the components of a previous row assembled in the stacker component 20 and help hold them in place. The contact tab 44 fits between the block tabs 23, with the block tabs 23 extending beyond corresponding ends of the contact tab 44 and exposing a flat outer contact surface 43, as shown in FIG. 1. If the contact block 40 is part of the last row of the device 1, the second cylindrical portion 42 is instead received by (mates with) the groove 51 of the end cap 50.

Hence, for the example embodiment, each stacker component 20 (each with three holes/voids) is associated with a plurality (three each in the example embodiment) of seals 30, three contact blocks 40, and three springs 5, to create a row (layer). An alternative embodiment to support 24 channels having two columns to support two electrode pins 200, utilizing 12 rows of components (using a dual hole/void setscrew block, end cap, & stacker components and having two seals/contact blocks/springs per row), is also contemplated as a practical solution. Of course, the number of channels of the two column approach can be adjusted to more or less than 24 by adjusting the number of rows.

FIG. 3 shows the example construction of an arbitrary number of individual rows of the example contact assembly into a complete example device. The complete device has a setscrew block 10 at one end, an end cap 50 at the other end, with "n" rows between them. A first row "a" is formed next to the setscrew block utilizing a first stacker component 20a with its three grooves 26 (see FIG. 5) mating with the corresponding three ring tabs 11 of the setscrew block 10. Three seals 30a are placed within the stacker component 20a at the locations as described above, and then three contact blocks 40a each with associated springs 5a inserted therein are mated with the stacker component 20a also in the manner described above. This forms the first row "a".

A second row is formed by adding an additional stacker component 20b, where each of the grooves 26 of the additional stacker component are each associated with a corresponding one of the contact blocks 40a as described above. This second stacker component 20b is then provided with three seals 30b, and three contact blocks 40b with associated springs 5b inserted therein to form a second row "b". This layering can then be repeated until the desired number "n" of rows is obtained, using "n" stacker components, and "n" sets of three seals, contact blocks, and springs. The final "capping" is done by using an end cap 50 to cover the final set of contact blocks by mating with the end cap with the last row of contact blocks.

As described above, the end cap 50 is provided, in the example embodiment, with a set of receiving grooves 51 like the receiving grooves 26 of the stacker component (see FIG. 2) to cap the end of the contact assembly my mating with the second cylindrical portions 42 of the last row of contact blocks 40n. The end cap 50 is also provide with a set of three bores/depressions 55 for receiving the ends (tips) 205 of the three pins 200 (see FIGS. 7, 9). Other than being adapted to receive the tips of the pins 200, the bores 55 should be sealed by the end cap 50 to prevent, as best possible, bodily fluids from seeping into the assembly.

The setscrew block 10 is provided, in the example embodiment, with the set of 3 ring tabs 11 (see FIGS. 3-4) that fit into the receiving grooves 26 of the stacker component 20. The stacker component 20 is also provided with three pin holes (bores) 12 for receiving the contact pins 200 therethrough (see FIG. 7, discussed below).

For the example embodiment of FIG. 1, the number of layers (rows) is chosen to be 8 (n=8), such that there are 8 rows (layers) of sets of 3 contact blocks placed in series, although any desired number of contact blocks could be accommodated by changing this arrangement (such as by using more or fewer layers and/or by having more or fewer than 3 blocks per row). Thus, in the example embodiment of FIG. 1, 24 contact blocks 40 are provided for accommodating 24 connections, such as might be used in an IPG device having 24 channels (or 25 if the IPG case itself acts as a channel), for example. The choice of three sets of contact blocks (3 columns) in 8 serial rows are used to accommodate 3 pins 200, with each contact pin 200 having eight conductive rings 202, as shown in FIG. 7. Each of the pins 200 in this example will therefore accommodate 8 separate conductive paths, such as to 8 electrodes, for example.

Figure 10:
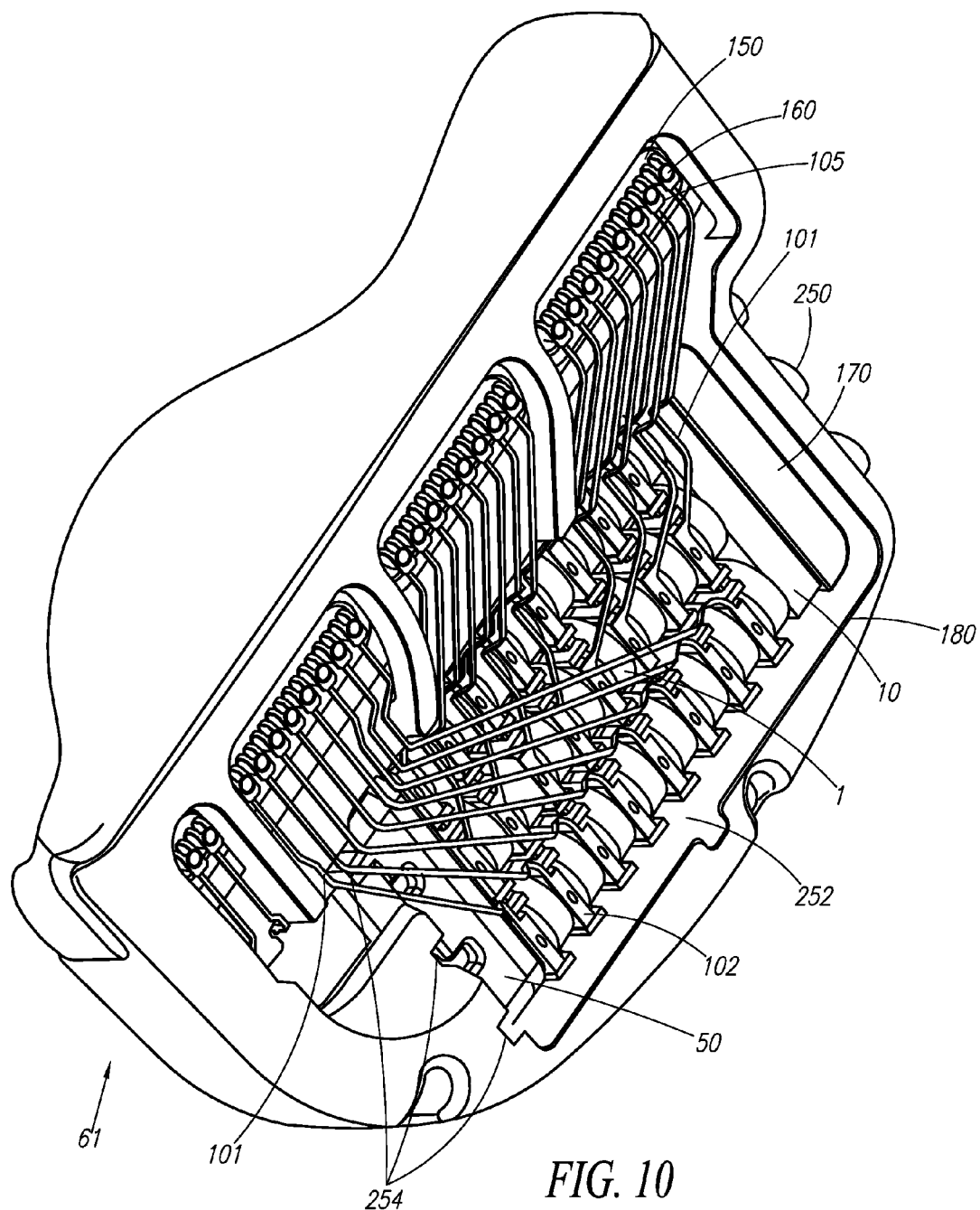
FIG. 10 shows the contact assembly of FIG. 6 installed in an IPG.

FIG. 6 shows the contact assembly of the example embodiment connected to three sets (groups) of lead frames 100, each having 8 leads 101, with each lead 101 having an end 102 adapted for being attached to the exposed outer contact surface 43 of a corresponding contact tab 44 (see, e.g., FIG. 4) and having a weld point 103. The leads 101 are conveniently routed in an organized manner around the tabs and other components of the stacker components to avoid shorting any of the leads together. Each of the leads 101 has a connector 105 at the other one end for connecting to a corresponding electrical connection point 160 on the IPG (as shown in FIG. 10). Thus, a conductive path is provided from one point 160 on the IPG, to the lead connector 105 connected to the point 160, down the associated lead 101 to the other end 102 to the corresponding contact block 40 to which the end 102 is connected, through the contact block to the associated spring 5 inserted therein, and on to the corresponding conductive ring 202, in contact with the spring 5, of the pin 200 inserted through that contact block 40, and ultimately to an electrode, such as might be implanted near the spine of a patient for providing pulse therapy.

As shown in example of FIG. 7, three bores (columns) are defined through each of the eight rows of example contact assembly 1, with each of the bores/columns for receiving the corresponding one of the pins 200 (thereby supporting three pins of eight conductors each). Each of the bores is defined by the appropriate axial alignment of one of the holes 12 provided through the setscrew block 10, the hole (33) of one of the seals (30) in each row (inserted in its corresponding contact holder 25), and the hole (center) of one of the springs 5 (that are inserted in their corresponding of the contact block 40) in each row, and finally to one of the bores 55 of the end cap 50, in a manner sufficient to ensure that the pins are adequately held in place and provide the appropriate electrical contacts to the associated contact blocks.

The setscrew block 10 is preferably comprised of titanium, although it could be comprised of any strong biocompatible metal such as stainless steel, nickel alloys, etc. The block can be manufactured using a machining process, or a metal injection molding (MIM) process, for example. The setscrew block holds setscrews (not shown) that tighten on the pins 200 setscrew rings and prevent the leads from moving out of alignment with the contacts and seals of the contact assembly. The setscrew block 10 has a set of three screws (not shown) that are used to set (fix) the pins 200 in place, once inserted, although other means of fixing the pins in place could be utilized, or the pins may be kept in place solely by friction contact with the seals and springs through which they pass, or by some other mechanism.

Each of the stacker components 20 is preferably comprised of a polymer such as Polysulfone, but it could be any biocompatible polymer or other composition of similar capability. The components 20 can be manufactured by using Injection molding, or a machining process suitable for its composition and size. The stacker components 20 hold the seals 30 and contact blocks 40 in alignment (axially and radially), control seal compression, and act as a precision spacer to maintain contact to contact pitch. In the example embodiment, the stack pitch is about 0.100" nominal and accepts a pin of about 0.055" nominal diameter. This concept will work down to around 0.080" pitch and pretty much any diameter (limited by how small the toroidal springs can be wound). The tolerance in the stacker contributes to the overall stack tolerance, likewise each of the seals is can be compressed as a separate assembly, so compression is controlled by the tolerances in one contact block and one seal not by the stack in its entirety.

Each of the seals 30 is preferably comprised of an elastic material such as silicone, or another elastomeric biocompatible polymer, and can be manufactured by molding, for example. Alternatively, the seals could be molded directly onto the stackers so they would form a single piece. The seals align with nonconductive segments 203 between the contact points on the pin 200 and conform to the pin surface so that even if flooded with conductive liquid in the lead bore, adjacent contacts have a sufficiently high enough impedance (e.g., 50 k Ohms) between them that they cannot effectively communicate electrically.

Each of the contact blocks 40 is preferably comprised of an MP35N alloy (a commercially available nonmagnetic, nickel-cobalt-chromium-molybdenum alloy that has a unique combination of properties), although any conductive biocompatible metal or alloy could be used. The contact blocks 40 can be manufactured by using a metal injection molding (MIM) process, or machined using known machining methods. The contact blocks are used to make electrical contact with the springs 5, transfer electrical signals from the pins 200 to the leads 101, form a weld surface for the leads 101, and compress the seals 30 (in conjunction with the stackers components 20).

The springs 5 are comprised of a small diameter (e.g., 0.0035" or less) coiled Pt—Ir wire joined into a continuous toroidal shaped helix. The assembly can be made compatible with, and thus utilize, springs such as those disclosed in U.S. Pat. Nos. 6,749,358 and 7,070,455, and U.S. Pat. App. Pub. No. 2008/0246231, incorporated herein by reference.

The end cap 50 is preferably comprised of the same or similar material discussed for the stacker components 20. Alternatively, the end cap 50 could be comprised of a biocompatible metal with the inclusion of additional seals to ensuring sealing, in particular where a conductive end cap might be desirable. The end cap forms the end of the pin bores and the depth of the holes 55 providing in the end caps (for receiving the end of the pins 200) registers the location where the pins align with the rest of the stack.]

The contact assembly 1, with reference to FIGS. 6, 7, and 10, can be assembled on assembly pins, such as the pins 200 or by using other pins of the appropriate size for aid in arranging the assembly components. For the example embodiment shown in the figures, one pin is used through each one of the three bores. The pins help to maintain alignment in the stack and make the components and the stack easier to handle. For the example embodiment, the assembly is accomplished manually by hand, but could be automated where mass production is contemplated to cover the cost of the machine and robotics.

The assembled contact assembly with pins therein is placed into a shell or housing 180. The shell has a feature (including the slots 254 of FIG. 10) that interlocks with the end cap tabs 56 on one side, including a vertical wall that forms a hard stop for the end cap 50. The other side of the shell 180 has an elastomeric piece 170 through which the bores continue through the cylinders 250. The assembly pins are inserted through the cylinders 250 of the elastomeric piece 170 first, then the curved and angled surfaces of the shell 180 and end cap 50 allow the rest of the stack to be pushed into place. Now the contact stack is trapped in alignment between the hard stop at the end cap 50 and the elastomeric piece 170 which serves as a spring to hold the stack in compression. The assembly pins can then be removed. The shell can then be attached to the IPG (or possibly was pre-attached). Then the lead frames 100 are attached to the IPG and the contact blocks, with the leads 101 being welded or soldered to the contact tab 43 at weld/solder point 103 (see FIG. 6). Then the shell is filled with a potting material 252, such as silicone, for example The potting material 252 surrounds the contact assembly and each of the leads and the IPG connection points to insulate the contact assembly electrically and physically hold the components in alignment to one another and binds the assembly together.

FIG. 8 shows an example multi-contact pin 200 as is used in the industry that has a plurality of conductive portions on its surface, such as contact rings 202 (8 are shown in the example) that are typically comprised of platinum, separated by insulating lead polymer portions 203. The pin has a setscrew ring comprised of MP35N alloy for being set in the setscrew block using a corresponding set screw.

For the example embodiment of FIG. 1, three contact pins 200 can be inserted into the contact assembly 1 as shown in FIG. 7. A close-up of a cross section of the contact assembly 1 with pins inserted is shown in FIG. 9. The components are arranged such that each spring 5 is in contact with a corresponding contact ring of one of the pins 200, such that an electrically conductive path runs from an internal lead of the pin (not shown) to the corresponding ring, to the corresponding spring, and then to the corresponding contact block, and through the block to the corresponding lead welded to the contact block to its connector and thereby to the IPG.

The entire contact assembly is arranged such that the insertion of the pins 200 into the contact blocks 40 cause a deformation of the springs 5 (e.g., cantering) to ensure a good electrical contact. The seals help to isolate and insulate the contacts from one another, including the prevention of fluids from providing an electrical path along the pin. The stacker components provide a convenient means of stacking the contact blocks in a tight, organized and compact manner, and thus helps to hold the components tightly in place.

FIG. 10 shows an example IPG 61 utilizing the contact assembly 1 with all components assembled together. The connectors 105 of the contacts are electrically connected to the IPG internal components via connecting pins 160 on the IPG, using three lead frames to provide a total of 24 connections between the stack assembly and the IPG. Thus, the use of 3 pins of 8 contacts each will provide the possible connection of 24 electrodes to the IPG.

Figure 11:
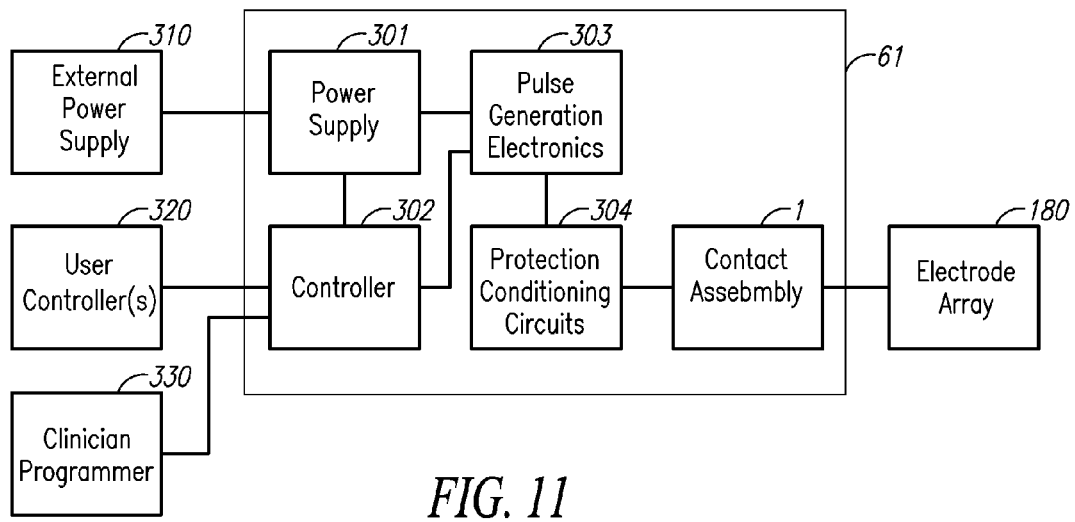
FIG. 11 is a block diagram showing example components of a pulse stimulation system using the example contact assembly.

FIG. 11 provides a block diagram of an example system including an IPG 61 that could utilized the contact assembly 1. The IPG 61 can be comprised of an internal power supply 301 (that may include a rechargeable battery), a controller 302, pulse generation electronics 303, protection/conditioning circuits 304, and the contact assembly 1 for connecting to an electrode array 180. The IPG 61 can be supported by an external power supply 310 (such as for charging the battery of the internal power supply 301), and a clinician programmer 330 and a user controller 320.

Figure 12:
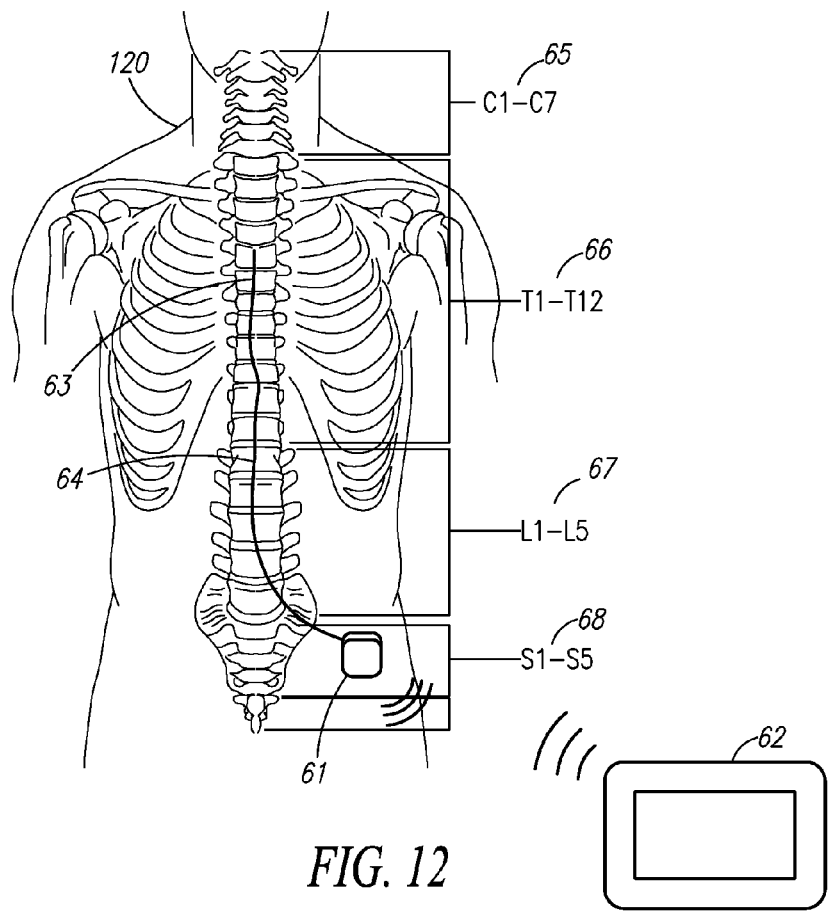
FIG. 12 is a diagram illustrating an example medical application of the pulse stimulation system of FIG. 11.

FIG. 12 shows an example application of the stimulator system for providing spinal stimulation. In that figure, the IPG 61 is shown implanted in a patient. Also shown is the human spine comprising the C1-C7 cervical vertebrae 65, the T1-T12 thoracic vertebrae 66, the L1-L5 lumbar vertebrae 67, and the S1-S6 sacral vertebrae 68. Electrodes 63 are shown disposed at the distal end of the spine and are positioned near the thoracic vertebrae 66. The Electrodes 63 are attached to the IPG 61 via electrode leads 64.

The leads and electrodes may be positioned anywhere along the spine to deliver the intended therapeutic effects of spinal cord electrical stimulation in the desired region of the spine. The distal end of the lead with its accompanying electrodes may be located along the epidural space and adjacent a desired portion of the spinal cord using well-established and known techniques for implanting and positioning SCS leads and electrodes, and the IPG 61 may be programmed using a clinician or other type of programmer 62 (such as a patient controller), as desired (and further described above). The electrode leads 64 can be connected to the IPG via a contact assembly as described in this application.

Many other example embodiments of the invention can be provided through various combinations of the above described features. Although the invention has been described hereinabove using specific examples and embodiments, it will be understood by those skilled in the art that various alternatives may be used and equivalents may be substituted for elements and/or steps described herein, without necessarily deviating from the intended scope of the invention. Modifications may be necessary to adapt the invention to a particular situation or to particular needs without departing from the intended scope of the invention. It is intended that the invention not be limited to the particular implementations and embodiments described herein, but that the claims be given their broadest reasonable interpretation to cover all novel and non-obvious embodiments, literal or equivalent, disclosed or not, covered thereby.

What is claimed is:

1. A contact assembly for an implantable medical device comprising:
   a first component forming an interior open portion therethrough, said first component having a first contact block receiving portion;
   a compliant insulating seal having a seal bore therethrough and being entirely contained within the interior open portion of said first component;
   a conductive contact block having a first side received by said first contact block receiving portion of said first component and in contact with said seal, said contact block also having a second side and a contact portion on a surface thereof and further having an interior open portion; and
   a second component having a second contact block receiving portion for receiving said second side of said contact block, said second component also having a bore therein, wherein
   said contact assembly is arranged for receiving a pin through said first component, through the bore of said seal, through the interior open portion of said conductive contact block, and into the bore of said second component, such that a conductive portion of said pin is provided in electrical contact with said conductive contact block when said pin is seated in said contact assembly.

2. The contact assembly of claim 1, wherein said first component has a plurality of additional interior portions each corresponding to an additional insulating seal and an additional contact block and wherein said second component has a plurality of additional bores corresponding to said plurality of additional interior portions for receiving a corresponding plurality of additional pins.

3. The contact assembly of claim 1, further comprising:
   an additional conductive contact block;
   an additional seal; and
   a third component having a third contact block receiving portion and bore therein, wherein
   said bore of said second component is adapted to be an additional interior portion for receiving said additional seal entirely therein, and wherein
   said second component includes an additional contact block receiving portion for receiving the first side of said additional contact block, and wherein
   the second side of said additional contact block is received by said third contact block receiving portion of said third component, and wherein
   said contact assembly is arranged for receiving said pin such that another conductive portion of said pin is provided in electrical contact with said additional contact device when said pin is seated in said contact assembly.

4. The contact assembly of claim 1, wherein said contact assembly is organized such that at least 24 of said contact blocks are arranged to support at least 3 of said pins for providing the at least 24 stimulation channels.

5. A contact assembly for an implantable medical device having at least 24 stimulation channels, said contact assembly for connecting to a plurality of pins each having a plurality of separate electrical contact surfaces, said contact assembly comprising:
   a plurality of conductive contact devices each adapted for electrically contacting one of the contact surfaces of one of the plurality of pins; and
   a plurality of conductive contact blocks each having an interior open portion adapted for receiving a corresponding one of said plurality of conductive contact devices in electrical contact therewith, wherein
   said conductive contact blocks are arranged into a series of rows such that each one of said rows has an equal number of contact blocks arranged side-by-side, and wherein
   said contact blocks are arranged such that each one of the contact blocks of one row are arranged with a corresponding one of the contact blocks of a subsequent and/or previous row to form a plurality of columns of contact blocks such that the interior open portions of the contact blocks of any given column are axially aligned to receive one of the plurality of pins, and wherein
   said contact assembly is organized such that at least 24 of said contact blocks are arranged to support at least 2 of said pins for providing the at least 24 stimulation channels.

6. The contact assembly of claim 5, where each of said contact blocks includes a tab having a flat contact portion on a surface thereof for connecting to an electrical lead.

7. The contact assembly of claim 5, wherein at least one of said contact devices is a toroidal spring forming a hole in the center of the spring for receiving a corresponding one of said pins and for contacting exactly one of the contact surfaces of the corresponding pin.

8. The contact assembly of claim 5, further comprising at least one stacking component for each one of said rows, each one of said stacking components having a plurality of first receiving portions, such that each one of said first receiving portions is adapted for mating with at least a first portion of a contact block.

9. The contact assembly of claim 8, wherein each one of said stacking components also has a plurality of second receiving portions, such that each one of said second receiving portions is adapted for mating with at least a second portion of a contact block.

10. The contact assembly of claim 9, wherein each one of the first receiving portions of at least one of said stacking components corresponds with a respective one of said contact blocks for receiving the first portion of said respective one of said contact blocks therein, and wherein each one of the second receiving portions of said at least one of said stacking components corresponds with a different respective one of said contact blocks for receiving the second portion of said different respective one of said contact blocks therein.

11. The contact assembly of claim 10, wherein for a second one of said stacking components, all of the plurality of first receiving portions of the second one of said stacking components does not receive any first portion of any of the plurality of contact blocks, and wherein for a third one of said stacking components, all of the plurality of second receiving portions of the third one of said stacking components does not receive any second portion of any of the plurality of contact blocks.

12. The contact assembly of claim 8, further comprising a plurality of compliant insulating seals having a seal bore therethrough each being associated with and in contact with one of said contact blocks and being contained in an interior portion of one of said stacking components.

13. The contact assembly of claim 5, further comprising a plurality of compliant insulating seals having a seal bore therethrough each being associated with and in contact with one of said contact blocks.

14. A contact assembly for an implantable medical device comprising:
   a plurality of stacking components each forming an interior open portion therethrough, each of said stacking components having a first contact block receiving portion on a first side and also having a second contact block receiving portion on a second side;
   a plurality of compliant seals, each of said seals having a seal bore therethrough and being entirely contained in the interior open portion of one of said stacking components; and
   a plurality of conductive contact blocks each having a first side for being received by the first contact block receiving portion of one of said stacking components and/or having a second side for being received by the second contact block receiving portion of another one of said stacking components, each one of said contact blocks having an interior open portion adapted for receiving one of said plurality a conductive contact devices therein, wherein
   said plurality of said stacking components are arranged in a series of rows, and wherein
   for each stacking component in one row following a preceding stacking component in a previous row, the first contact block receiving portion is mated with the first side of one of the plurality of contact blocks having its second side mated with the second contact block receiving portion of the preceding stacking component in the previous row.

15. The contact assembly of claim 14, wherein said each one of said contact blocks includes a conductive contact device provided in the interior open portion thereof, said conductive contact device adapted to form a hole in the center of the spring for receiving a conductive portion of a pin.

16. The contact assembly of claim 14, wherein at least 24 contact blocks are provided to support at least 24 channels of the implantable medical device.

17. A contact assembly for an implantable medical device comprising:
   a setscrew block having a bore therethrough forming a first end of said assembly;
   a plurality of stacking components each forming an interior open portion therethrough, each of said stacking components having a first contact block receiving portion on a first side and also having a second contact block receiving portion on a second side;
   a plurality of compliant seals, each of said seals having a seal bore therethrough and being entirely contained in the interior open portion of one of said stacking components;
   a plurality a conductive contact devices;
   a plurality of conductive contact blocks each having a first side for being received by the first contact block receiving portion of one of said stacking components and/or having a second side for being received by the second contact block receiving portion of another one of said stacking components, each one of said contact blocks having a contact portion on a surface thereof and having an interior open portion adapted for receiving one of said plurality a conductive contact devices therein; and an end cap including a bore forming a second end of said assembly.

18. The contact assembly of claim 17, wherein the plurality of said stacking components are arranged in a series of rows such that for each stacking component in one row following a preceding stacking component in a previous row, the first contact block receiving portion is mated with the first side of one of said contact blocks having its second side mated with the second contact block receiving portion of the preceding stacking component in the previous row, and wherein the second contact block receiving portion of the first contact block in the series mates with an inner end of said setscrew block, and further wherein the end cap mates with the second end of the contact block having its first end mated with the last stacking component in the series.

19. The contact assembly of claim 17, wherein at least 24 contact blocks are provided to support at least 24 channels of the implantable medical device.

20. A contact assembly for an implantable medical device comprising:

a stacking component forming a plurality of interior open portions therethrough, each interior open portion having a corresponding contact block receiving portion;

a plurality of compliant seals having a seal bore therethrough, each of said seals being entirely contained within a corresponding one of said interior open portions of said first stacking component;

a plurality of conductive contact blocks each for mating with one end of a corresponding one of said contact block receiving portions and having a contact portion on a surface thereof, wherein each one of said conductive contact blocks has an interior open portion therein; and a setscrew block having a plurality of setscrew bores therethrough such that each setscrew bore corresponds to one of said interior open portions of said stacking component, wherein each one of said stacking component interior open portions is formed in alignment with the seal bore of the corresponding seal, the interior open portion of the corresponding contact block, and the corresponding setscrew bore to form a continuous axial chamber adapted for receiving a respective pin inserted from outside of said contact assembly, with said respective pin having a contact surface portion thereon for electrically connecting to the respective contact block.

21. The contact assembly of claim 20, each of said contact blocks further comprising an interior open portion adapted for receiving a conductive contact device therein, each of said contact devices having a central open portion therethrough, wherein the central open portion of each contact device is for receiving the respective pin and for contacting the conductive surface of the respective pin for forming an electrical conductive path from the contact portion of said each contact device to the contact surface of the respective pin.

22. The contact assembly of claim 20, comprising a plurality of said stacking components arranged in rows for accommodating a plurality of contact surfaces on each said pin.

23. The contact assembly of claim 20, wherein at least 24 contact blocks are provided to support at least 24 channels of the implantable medical device.

24. A contact assembly for an implantable medical device comprising:

a setscrew block having a plurality of setscrew bores therethrough forming a first end of said assembly;

a plurality of stacking components arranged into a series of rows, each one of said stacking components having a plurality of interior open portions therethrough with each one of said interior open portions being associated with one of said setscrew bores and forming a first contact block receiving portion on a first side and also forming a second contact block receiving portion on a second side;

a plurality of compliant seals each having a seal bore therethrough and each being provided in a corresponding one of said interior open portions of a corresponding one of said stacking components;

a plurality a conductive contact devices;

a plurality of conductive contact blocks each having a first side for being received by one of said first contact block receiving portions of one of said stacking components and/or having a second side for being received by one of said second contact block receiving portions of another one of said stacking components, each one of said contact blocks having a contact portion on a surface thereof and having an interior open portion adapted for receiving one of said plurality of conductive contact devices therein, wherein each one of said interior open portions of each one of said conductive contact blocks is associated with one of said setscrew bores; and an end cap including a plurality of end bores forming a second end of said assembly, each one of said end bores being associated with one of said setscrew bores, wherein said contact assembly is adapted for receiving a plurality of pins, each one of said pins for being inserted into an associated one of said setscrew bores and through the interior open portions of the stacking components, the seal bores, and the interior portions of the contact blocks associated therewith, with the end of each pin entering the associated one of said end bores.

25. The contact assembly of claim 24, wherein the plurality of said stacking components are arranged in a series of rows such that for each stacking component in one row following a preceding stacking component in a previous row, the first contact block receiving portion is mated with the first side of one of said contact blocks having its second side mated with the second contact block receiving portion of the preceding stacking component in the previous row, and wherein the second contact block receiving portion of the first contact block in the series mates with an inner end of said setscrew block, and further wherein the end cap mates with the second end of the contact block having its first end mated with the last stacking component in the series.

26. The contact assembly of claim 24, wherein at least 24 contact blocks are provided to support at least 24 channels of the implantable medical device.

27. A contact assembly for an implantable medical device for providing at least 24 stimulation channels, said contact assembly comprising:

a setscrew block having a plurality of setscrew bores therethrough forming a first end of said assembly;

a plurality of stacking components arranged into a series of rows, each one of said stacking components having a plurality of interior open portions therethrough with each one of said interior open portions being associated with one of said setscrew bores and forming a first contact block receiving portion on a first side and also forming a second contact block receiving portion on a second side;
a plurality of compliant seals each having a seal bore therethrough and each being entirely contained in a corresponding one of said interior open portions of a corresponding one of said stacking components;
a plurality of at least 24 conductive contact devices;
a plurality of at least 24 conductive contact blocks each having a first side for being received by one of said first contact block receiving portions of one of said stacking components and/or having a second side for being received by one of said second contact block receiving portions of another one of said stacking components, each one of said contact blocks having a contact portion on a surface thereof and having an interior open portion adapted for receiving one of said plurality of conductive contact devices therein, wherein each one of said interior open portions of each one of said conductive contact blocks is associated with one of said setscrew bores; and
an end cap including a plurality of end bores forming a second end of said assembly, each one of said end bores being associated with one of said setscrew bores, wherein
the plurality of said stacking components are arranged in a series of rows such that for each stacking component in one row following a preceding stacking component in a previous row, the first contact block receiving portion is mated with the first side of one of said contact blocks having its second side mated with the second contact block receiving portion of the preceding stacking component in the previous row, and further wherein
the second contact block receiving portion of the first contact block in the series mates with an inner end of said setscrew block, and wherein
the end cap mates with the second end of the contact block having its first end mated with the last stacking component in the series, and wherein
said contact assembly is adapted for receiving a plurality of pins, each one of said pins having a plurality of contact surface portions thereon, and each one of said pins for being inserted into an associated one of said setscrew bores and through the interior open portions of the stacking components, the seal bores, and the interior portions of the contact blocks associated therewith, with the end of each pin entering the associated one of said end bores, and with each of the conductive contact devices being adapted for electrically connecting to a corresponding one of the contact surface portions of one of the pins.

28. A stimulation system comprising a contact assembly according to claim 27 and having at least 24 channels for stimulating at least one stimulation region of a patient, said system, said system further comprising:
an implantable pulse generation device (IPG) adapted to be implanted in the patient, said IPG including:
a storage device,
a pulse generation circuit adapted for providing the at least 24 stimulation channels,
a plurality of at least 24 connectors for connecting each one of said contact blocks to a corresponding connection on said IPG;
an external device for wirelessly connecting to said IPG for controlling an operation of said IPG; and
an external energy transmitter for wirelessly providing electrical energy to said energy storage device.

29. A stimulation system having at least 24 stimulation channels for stimulating at least one stimulation region of a patient, said system comprising:
an implantable pulse generation device (IPG) adapted to be implanted in the patient, said IPG including:
a storage device,
a pulse generation circuit adapted for providing the at least 24 stimulation channels,
a contact assembly for connecting said pulse generation circuit to a plurality of pins, each one of said pins having a plurality of contact surfaces, each of said contact surfaces for electrically connecting to at least one of a plurality of electrodes, said contact assembly comprising:
a plurality of conductive contact devices each adapted for electrically contacting one of the contact surfaces of one of the plurality of pins, and
a plurality of at least 24 conductive contact blocks each having an interior open portion adapted for receiving a corresponding one of said plurality of conductive contact devices in electrical contact therewith, wherein
said conductive contact blocks are arranged into a series of rows such that each one of said rows has an equal number of contact blocks arranged side-by-side, and wherein
said contact blocks are arranged such that each one of the contact blocks of one row are arranged with a corresponding one of the contact blocks of a subsequent and/or previous row to form a plurality of columns of contact blocks such that the interior open portions of the contact blocks of any given column are axially aligned to receive one of the plurality of pins;
a plurality of at least 24 connectors for connecting each one of said contact blocks to a corresponding connection on said IPG;
an external device for wirelessly connecting to said IPG for controlling an operation of said IPG; and
an external energy transmitter for wirelessly providing electrical energy to said energy storage device.

30. A method of providing stimulation therapy to a patient using the system of claim 29.

* * * * *